(12) United States Patent
Broddegaard et al.

(10) Patent No.: US 7,974,791 B2
(45) Date of Patent: Jul. 5, 2011

(54) METHOD FOR THE OPTIMIZATION OF STRESS DISTRIBUTION IN ACOUSTIC THERMOGRAPHY APPLICATIONS

(75) Inventors: Mattias Broddegaard, Söderköping (SE); Christian Homma, Vaterstetten (DE); Max Rothenfusser, München (DE)

(73) Assignee: Siemens Aktiengesellschaft, Munich (DE)

( * ) Notice: Subject to any disclaimer, the term of this patent is extended or adjusted under 35 U.S.C. 154(b) by 231 days.

(21) Appl. No.: 12/361,695

(22) Filed: Jan. 29, 2009

(65) Prior Publication Data

US 2009/0204345 A1      Aug. 13, 2009

(30) Foreign Application Priority Data

Feb. 12, 2008   (DE) .......................... 10 2008 008 609

(51) Int. Cl.
*G01B 5/28* (2006.01)
(52) U.S. Cl. ....................................................... 702/35
(58) Field of Classification Search ...................... 702/35
See application file for complete search history.

(56) References Cited

U.S. PATENT DOCUMENTS

| | | | | |
|---|---|---|---|---|
| 5,269,181 | A * | 12/1993 | Gibson et al. | 73/160 |
| 2004/0089812 | A1 * | 5/2004 | Favro et al. | 250/341.6 |
| 2005/0151083 | A1 * | 7/2005 | Favro et al. | 250/341.6 |
| 2005/0167596 | A1 * | 8/2005 | Rothenfusser et al. | 250/341.6 |
| 2007/0045544 | A1 * | 3/2007 | Favro et al. | 250/341.6 |
| 2010/0138027 | A1 * | 6/2010 | Ostapenko | 700/110 |

FOREIGN PATENT DOCUMENTS

EP        1 582 867 A2    10/2005

* cited by examiner

*Primary Examiner* — Cindy Hien-Dieu Khuu
(74) *Attorney, Agent, or Firm* — King & Spalding L.L.P.

(57) ABSTRACT

In a method for the optimization of stress distribution on an object to be tested for flaws by ultrasound excitation and evaluation based on resulting surface temperature distribution,—a simulation is performed under test conditions on a CAD model of the object prior to a testing an object,—vibrational spectra and modal vibrational forms are calculated,—local mechanical stresses are determined from the vibrational modes, whereby—modes to be excited for the real test are selected from the entirety of the occurring modes such that,—the mechanical stress lies in a selected region above a predetermined minimum stress to enable a reliable proof of defect,—the mechanical stress in all other regions of the inspection part, in particular on easily damaged component structures, is smaller than a predetermined maximum stress by a predetermined factor, in order not to damage the component at weak points.

16 Claims, 4 Drawing Sheets

19750 Hz

24169 Hz

METHOD FOR THE OPTIMIZATION OF STRESS DISTRIBUTION IN ACOUSTIC THERMOGRAPHY APPLICATIONS

CROSS-REFERENCE TO RELATED APPLICATIONS

This application claims priority to DE Patent Application No. 10 2008 008 609.6 filed Feb. 12, 2008, the contents of which is incorporated herein by reference in its entirety.

TECHNICAL FIELD

The present application relates to acoustic thermography.

BACKGROUND

Acoustic thermography is a non-destructive testing method to prove defects in inspection parts of different sizes, materials and structure.

The inspection part is generally vibrated with high-performance ultrasound (typically >approx. 15 kHz, >approx. 100 W), which, on defects such as cracks or delaminations, is converted into heat by means of different effects. This local thermal response is registered and then evaluated with the aid of a thermal imaging camera. It may however result in local damage in the case of excessive vibrational amplitudes which preferably occur on thinner regions of the inspection part.

The conventional conversion of acoustic thermography takes place with approximately 20 kHz fixed frequency. In this process, the individual vibrational behavior of the individual inspection part is taken into consideration, whereby a relatively poor part-to-part reproducibility results on the one hand and the probability of local damage can neither be predicted nor reduced on the other hand. Crack formation and advances occur as soon as the yield point of the material is locally exceeded.

Attempts can currently be made using the following methods in order to prove that the technology described is non-destructive.
a) Serial measurements on a inspection part, with the risk of damaging a comparable part in a cycle being minimal if the inspection part was not damaged after n testing cycles. Since even components of the same type have slightly different vibrational spectra, it may be that one part is not damaged while another part is however locally damaged under the same test conditions.
b) Laser vibrometry examinations for determining the vibration of the inspection part. No statements relating to the loads of inner structures can however be made here.

EP 1 582 867 A2 discloses a method for instance, which operates with attunable exciters, with the aid of which the individual vibrational behavior of each individual inspection part can be taken into consideration. By exciting several resonance frequencies, a better part-to-part reproducibility is achieved at the same time as an increased degree of efficiency, since less electrical power is needed in the case of a resonant excitation in order to achieve an adequately high vibrational amplitude of the inspection part. The disadvantage of possible local damage, for instance at points with a minimal material thickness, still exists however.

SUMMARY

According to various embodiments, a method for acoustic thermography can be described, with which a component can be better reproducibly checked for flaws, in particular cracks or breakages, and at the same time no defects, which occur as a result of exceeding local characteristic values, are initiated or worsened in the component.

According to an embodiment, a method for the optimization of stress distribution on an object to be tested for defects using ultrasound excitation and evaluation on the basis of a resulting surface temperature distribution, may have the following steps:—performing a simulation on a Computer Aided Design (CAD) model of the object under test conditions prior to testing an object,—calculating vibrational spectra and modal vibrational forms,—determining local mechanical stresses from the vibrational modes in each instance, wherein—modes to be excited for the real test being selected from the entirety of the occurring modes such that—the mechanical stress lies in a selected region above a predetermined minimum stress in order to enable a reliable proof of defect, and—the mechanical stress in all other regions of the inspection part, in particular on easily damaged component structures, is smaller than a predetermined maximum stress by a predetermined factor in order not to damage the component at weak points.

According to a further embodiment, a finite element simulation method can be used to calculate vibrational spectra and modal vibrational forms. According to a further embodiment, all modes may be firstly calculated in the frequency range between approximately 15 and 25 kHz and the occurring mechanical stresses are calculated for these modes. According to a further embodiment, selected optimum resonance frequencies can be matched to the real component, by the vibrational spectra of the real component being measured and compared with the calculated spectrum of the model. According to a further embodiment, the vibrational spectrum of the real component may be measured by excitation with the ultrasound exciter in the case of a low output by detection with a vibrational sensor, for instance laser vibrometer. According to a further embodiment, the two spectra can be aligned by means of a correlation algorithm. According to a further embodiment, the site of coupling-in in for the ultrasound exciter can be adjusted to the component form.

BRIEF DESCRIPTION OF THE DRAWINGS

Exemplary embodiments are described below with reference to schematic figures, in which.

DETAILED DESCRIPTION

The various embodiments relate to the selection of optimal resonance frequencies from the plurality of resonance frequencies occurring, in order to further increase the local probability of detection of flaws and at the same time to minimize the probability of damage at weak spots.

According to an embodiment, a CAD model of the inspection part is examined and a finite element simulation program is used to calculate vibrational spectra and modal vibrational forms. The local mechanical stresses can in turn be calculated from the modes, wherefrom statements in respect of the non-destructiveness relating to the whole part can be derived (FIG. 1 to FIG. 4).

The point of coupling-in plays an important role since certain modes can be excited more or less effectively as a function hereof. The site of coupling-in can naturally also be optimized with the method described here.

The site of coupling-in for the ultrasound exciter is adjusted here in accordance with the component form.

All modes/vibrational forms in the frequency range of interest, for instance 15 to 25 kHz, are firstly calculated and the occurring mechanical stresses are calculated for these modes. These are subject to the following boundary conditions:

As proof of defects, certain minimum stresses are needed; the material is nevertheless destroyed as of a threshold stress.

The modes to be excited are now chosen in accordance with the following method, provided that only one selected region of the component to be tested is to be examined for defects. If this is not the case, a) is thus omitted, cf. FIGS. 1 and 2:

a) The stress in the selected region must lie above the minimum stress since no reliable proof of defect is otherwise possible, b) The mechanical stress in all other parts of the inspection part, in other words particularly on easily damaged component structures, must lie below a threshold stress by a predetermined factor in order not to damage the material.

As each real component now differs from the ideal CAD model, the optimum resonance frequencies thus found must be matched to the real part. The vibrational spectrum of the real part is measured, for instance by sweep excitation with the exciter in the case of a low output and detection with a vibrational sensor, for instance a laser vibrometer, and is compared with the calculated spectrum of the model.

The two spectra are aligned by means of a correlation algorithm. The previously calculated optimum frequencies are converted using the correction factors obtained therefrom. The converted actual excitation of the inspection part then takes place in the case of these corrected frequencies.

Figure 1:
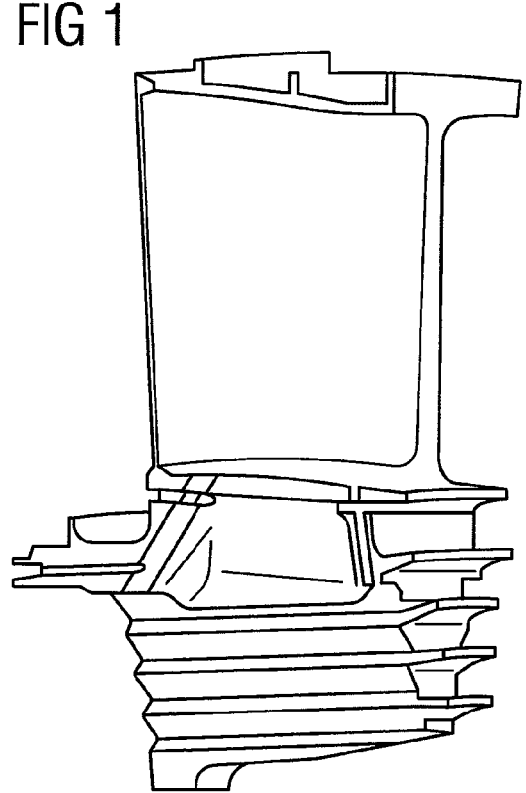
FIG. 1: shows in detail an imported CAD model, here a turbine blade.

FIG. 1 shows a representation of an imported CAD model, here a turbine blade, which is to be tested as a real structure.

Figure 2:
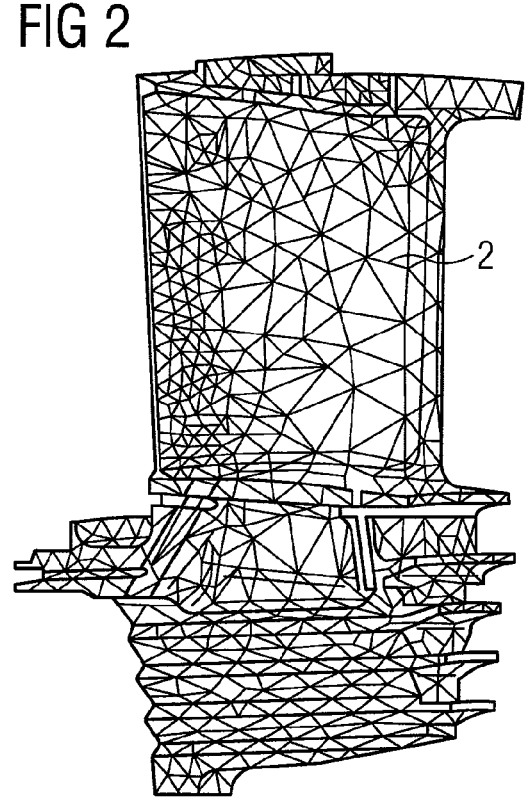
FIG. 2: shows in detail a netted model in the finite element simulation program.

In FIG. 2, a cross-linking (2) is present on the CAD model, which is applied to the model with the aid of a finite element simulation program.

Figure 3:
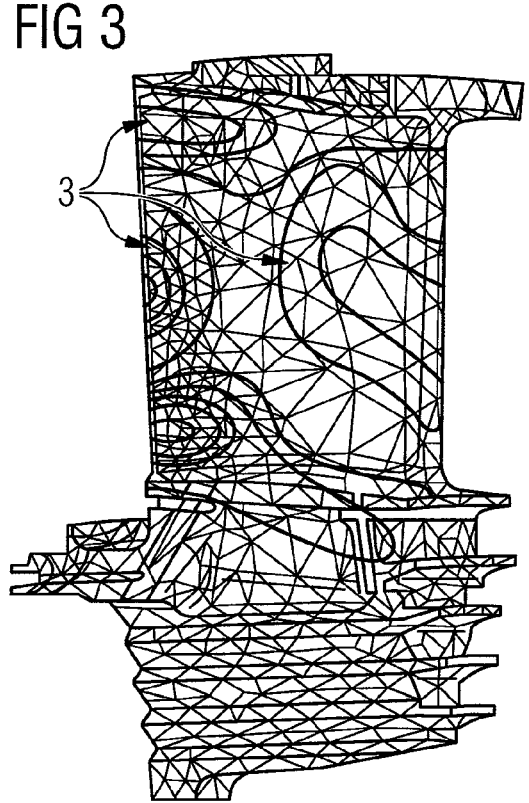
FIG. 3: shows in detail a calculated resonant vibrational form, also referred to as mode.

One of the calculated vibrational forms is shown in FIG. 3. It is also referred to as mode (3).

Figure 4:
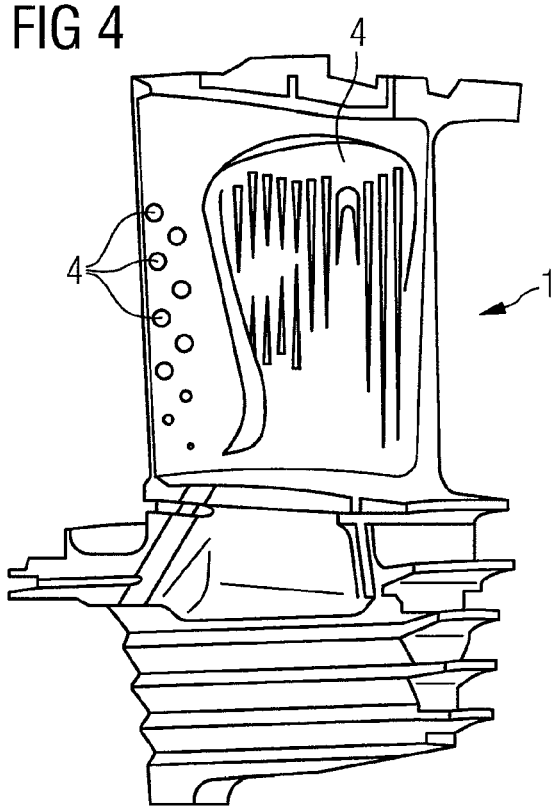
FIG. 4: shows in detail the mechanical stresses inside the component as calculated from FIG. 3, FIG. 5: shows in detail a favorable frequency, equivalent to a maximized stress in the region (A) in which defects are to be sought and moderate stress on fragile reinforcements (B).

The mechanical stresses (4) in the interior of the component which are determined from the modes are shown in FIG. 4.

Figure 5:
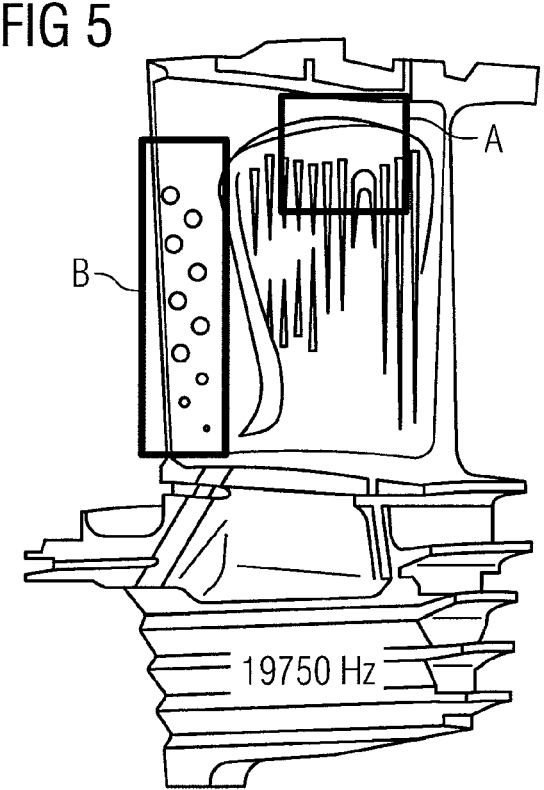

FIG. 5 shows a favorable frequency, with a maximized stress in the region in which defects are to be sought (A) and moderate stress on fragile reinforcements (B).

Figure 6:
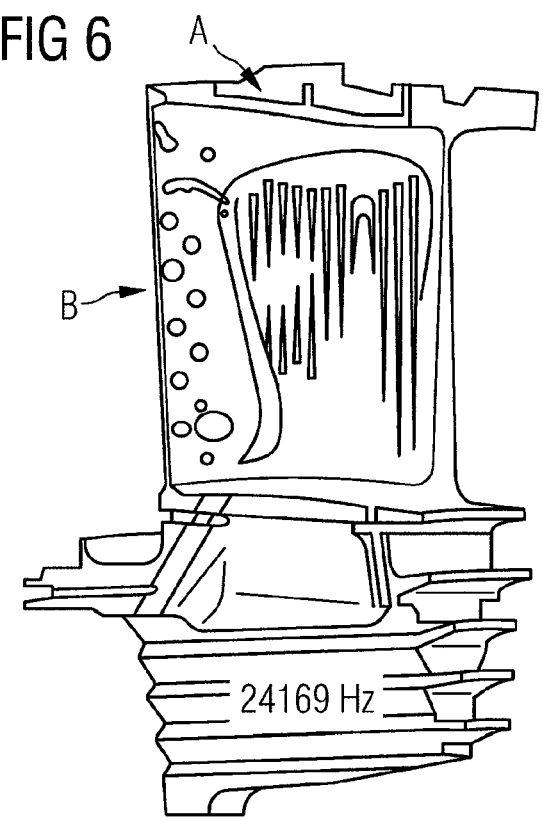
FIG. 6: shows in detail an unfavorable frequency equivalent to less stress in the region (A) in which defects are to be sought, but increased stress on fragile reinforcements (A).

FIG. 6 shows an unfavorable frequency, since stress barely occurs in the region (A) in which defects are to be sought, but excessive stress on fragile reinforcements (B).

Figure 7:
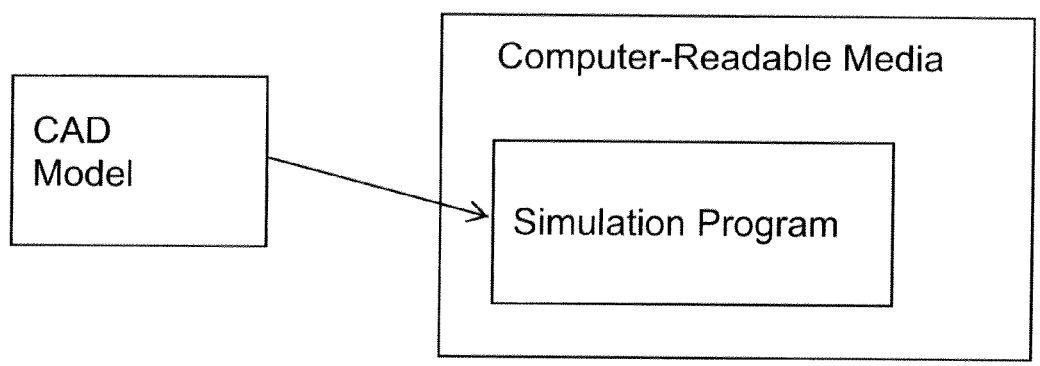
FIG. 7 shows a system for optimization of stress distribution on an object to be tested for defects using ultrasound excitation and evaluation based on a resulting surface temperature distribution.

FIG. 7 shows a system for optimization of stress distribution on an object to be tested for defects using ultrasound excitation and evaluation based on a resulting surface temperature distribution. The system includes a simulation program embodied in non-transitory computer readable media for: performing a simulation on a Computer Aided Design (CAD) model of the object under test conditions prior to testing an object, calculating vibrational spectra and modal vibrational forms, and determining local mechanical stresses from the vibrational modes in each instance.

What is claimed is:

1. A computer program for optimization of stress distribution on an object to be tested for defects using ultrasound excitation and evaluation based on a resulting surface temperature distribution, the computer program embodied in non-transitory computer readable media and operable when executed by a processor to perform the following steps:

performing a simulation on a Computer Aided Design (CAD) model of the object under test conditions prior to testing the object, calculating vibrational spectra and a plurality of vibrational modes, determining local mechanical stresses on the simulated object resulting from each of the plurality of vibrational modes, and selecting vibrational modes to be excited for an actual, non-simulation test of a real object from the plurality of vibrational modes such that:

mechanical stress in a selected region of the real object resulting from each selected vibrational mode is above a predetermined minimum stress in order to enable a reliable proof of defect, and mechanical stress in all other regions of the real object resulting from each selected vibrational mode is smaller than a predetermined maximum stress by a predetermined factor in order not to damage the real object at weak points.

2. The computer program according to claim 1, wherein the all other regions of the real object are easily damaged component structures.

3. The computer program according to claim 1, wherein a finite element simulation method is used to calculate the vibrational spectra and the plurality of vibrational modes.

4. The computer program according to claim 1, wherein the plurality of vibrational modes are firstly calculated in a frequency range between approximately 15 and 25 kHz and occurring mechanical stresses are calculated for each vibrational mode.

5. The computer program according to claim 1, wherein one or more resonance frequencies are matched to the real object, by measuring vibrational spectra of the real object and comparing the measuring vibrational spectra with the calculated spectra of the model.

6. The computer program according to claim 5, wherein the vibrational spectra of the real component is measured by excitation with an ultrasound exciter and a vibrational sensor.

7. The computer program according to claim 5, wherein the two spectra measured vibrational spectra of the real object and the calculated spectra of the model are aligned by means of a correlation algorithm.

8. The computer program according to claim 6, wherein a site of coupling-in for the ultrasound exciter is adjusted based on a form of the real object component.

9. A system for optimization of stress distribution on an object to be tested for defects using ultrasound excitation and evaluation based on a resulting surface temperature distribution, comprising:

means for performing a simulation on a Computer Aided Design (CAD) model of the object under test conditions prior to testing the object, means for calculating vibrational spectra and a plurality of vibrational modes, means for determining local mechanical stresses on the simulated object resulting from each of the plurality of vibrational modes, and means for selecting vibrational modes to be excited for an actual, non-simulation test of a real object from the plurality of vibrational modes such that:

mechanical stress in a selected region of the real object resulting from each selected vibrational mode is above a predetermined minimum stress in order to enable a reliable proof of defect, and mechanical stress in all other regions of the real object resulting from each selected vibrational mode is smaller than a predetermined maximum stress by a predetermined factor in order not to damage the real object at weak points.

10. The system according to claim 9, wherein the all other regions of the real object are easily damaged component structures.

11. The system according to claim 9, wherein a finite element simulation method is used to calculate the vibrational spectra and the plurality of vibrational modes.

12. The system according to claim 9, wherein the plurality of vibrational modes are firstly calculated in a frequency range between approximately 15 and 25 kHz and occurring mechanical stresses are calculated for each vibrational mode.

13. The system according to claim 9, wherein one or more resonance frequencies are matched to the real object, by measuring vibrational spectra of the real object and comparing the measuring vibrational spectra with the calculated spectra of the model.

14. The system according to claim 13, wherein the vibrational spectra of the real component is measured by excitation with an ultrasound exciter and a vibrational sensor.

15. The system according to claim 13, wherein the two spectra measured vibrational spectra of the real object and the calculated spectra of the model are aligned by means of a correlation algorithm.

16. The system according to claim 14, wherein a site of coupling-in for the ultrasound exciter is adjusted based on a form of the real object component.

* * * * *